(12) United States Patent
Grune et al.

(10) Patent No.: US 8,191,169 B2
(45) Date of Patent: Jun. 5, 2012

(54) ANTI-MICROBIAL COMPOUNDS USED IN GARMENTS FOR WATER BASED ACTIVITIES

(76) Inventors: Guerry L. Grune, Virginia Beach, VA (US); James Anonsen, Kahaihae, HI (US)

( * ) Notice: Subject to any disclaimer, the term of this patent is extended or adjusted under 35 U.S.C. 154(b) by 28 days.

(21) Appl. No.: 12/312,452

(22) PCT Filed: Nov. 10, 2007

(86) PCT No.: PCT/US2007/023666
§ 371 (c)(1),
(2), (4) Date: May 11, 2009

(87) PCT Pub. No.: WO2008/147395
PCT Pub. Date: Dec. 4, 2008

(65) Prior Publication Data
US 2010/0205709 A1 Aug. 19, 2010

Related U.S. Application Data

(60) Provisional application No. 60/857,836, filed on Nov. 10, 2006.

(51) Int. Cl.
B63C 11/04 (2006.01)
B63C 11/10 (2006.01)

(52) U.S. Cl. .................................. 2/2.16; 2/2.17; 2/2.15

(58) Field of Classification Search ............... 2/2.15, 2/2.16, 2.17
See application file for complete search history.

(56) References Cited

U.S. PATENT DOCUMENTS

| | | | | |
|---|---|---|---|---|
| 6,319,599 B1 * | 11/2001 | Buckley | | 428/308.4 |
| 6,984,265 B1 * | 1/2006 | Raguse et al. | | 117/73 |
| 7,134,929 B2 * | 11/2006 | Chen | | 441/102 |
| 7,506,651 B2 * | 3/2009 | Anonsen | | 128/859 |
| 7,538,159 B2 * | 5/2009 | Wang et al. | | 525/313 |
| 7,544,740 B2 * | 6/2009 | Wang et al. | | 525/94 |
| 7,560,510 B2 * | 7/2009 | Wang et al. | | 525/88 |
| 7,572,160 B2 * | 8/2009 | Halliday | | 441/64 |
| 7,572,855 B2 * | 8/2009 | Fudemoto et al. | | 524/445 |
| 7,579,398 B2 * | 8/2009 | Fudemoto et al. | | 524/445 |
| 7,649,049 B2 * | 1/2010 | Kleckner et al. | | 525/88 |
| 7,718,737 B2 * | 5/2010 | Wang et al. | | 525/313 |
| 7,829,624 B2 * | 11/2010 | Warren | | 524/505 |
| 2005/0008861 A1 * | 1/2005 | Yadav et al. | | 428/403 |
| 2005/0126338 A1 * | 6/2005 | Yadav | | 75/255 |
| 2005/0214553 A1 * | 9/2005 | Yannetti et al. | | 428/461 |
| 2006/0122544 A1 * | 6/2006 | Ciluffo | | 601/15 |
| 2006/0207610 A1 * | 9/2006 | Anonsen | | 128/859 |
| 2006/0207611 A1 * | 9/2006 | Anonsen | | 128/859 |
| 2007/0049678 A1 * | 3/2007 | Kim et al. | | 524/430 |
| 2007/0110909 A1 * | 5/2007 | Isakoff et al. | | 427/421.1 |
| 2007/0140951 A1 * | 6/2007 | O'Brien et al. | | 423/592.1 |

(Continued)

Primary Examiner — Bobby Muromoto, Jr.

(57) ABSTRACT

The invention includes compounds used to manufacture garments for use in water based activities that have a rubber, synthetic rubber, or neoprene compound. The compound is primarily polychloroprene or other suitable polymers and at least one metal of nanoparticle size. The compound composition includes a metal concentration that is sufficient to provide anti-bacterial properties that retard or eliminate bacterial growth on any surface of the composition used to produce the garment. The composition may include a sub-micron metal composition including sub-micron sized silver, zinc oxide, aluminum oxide and boron nitride particles as well as a polyol ester, wherein the thermal conductance of the aforementioned submicron composition is >350,000 W/m$^{2\circ}$ C. for a 0.001 inch layer of the aforementioned metal composition, the thermal resistance is <0.0045° C.-in$^2$/Watt for a 0.001 inch layer of the aforementioned metal composition, and the average particle size is <0.49 microns for a <0.000020 inch layer of the aforementioned metal composition.

13 Claims, 2 Drawing Sheets

U.S. PATENT DOCUMENTS

| | | | |
|---|---|---|---|
| 2007/0170393 A1* | 7/2007 | Zhang | 252/183.13 |
| 2007/0199729 A1* | 8/2007 | Siegel et al. | 174/73.1 |
| 2008/0219938 A1* | 9/2008 | Grune | 424/59 |
| 2008/0219939 A1* | 9/2008 | Grune | 424/59 |
| 2008/0233060 A1* | 9/2008 | Grune | 424/59 |
| 2009/0209629 A1* | 8/2009 | Mirkin et al. | 514/44 R |
| 2009/0214447 A1* | 8/2009 | Jennings et al. | 424/49 |
| 2010/0021894 A1* | 1/2010 | Mirkin et al. | 435/6 |

* cited by examiner

ANTI-MICROBIAL COMPOUNDS USED IN GARMENTS FOR WATER BASED ACTIVITIES

This application takes priority under 35 USC 119(e) from U.S. Provisional application No. 60/857,836, filed Nov. 10, 2006, entitled "ANTI-MICROBIAL COMPOUNDS USED IN GARMENTS FOR WATER BASED ACTIVITIES".

BACKGROUND

The present invention relates to water based activities attire and relates more particularly to compounds used to manufacture garments used for insulation that possess anti-microbial activity to guard against infections.

Often wearers of wetsuits and in some cases drysuits (and associated apparel needed for insulation) that have cuts or have other wounds find that infections occur rapidly or are exasperated when individuals are wearing the insulation apparel.

Common infections associated with this phenomenon may be aggravated due to *Pseudomonas auruginosa* (gram negative) or *Staphylococcus aureus* (gram positive) or by one or more of the thousands of other species of bacterium or mold that find the normal insulating materials (neoprene or polychoroprene, or synthetic rubber or variations thereof) good support substrates that harbor moisture/water and a food source, thereby allowing the undesired microorganisms to continue to multiply.

The use of colloidal or micronized and nano-sized silver has been found to retard and even eliminate bacteria or mold associated with human health hazards and more specifically with causing or prolonging infection. Other metals, such as platinum, paladium, nickel, gold, aluminum, iron, copper, selenium, tungsten, or an alloy of any combination of these metals also will retard bacterial growth. In this case the metals could be colloidal platinum, colloidal paladium, colloidal nickel, colloidal gold, colloidal aluminum, colloidal iron, colloidal copper, colloidal selenium, colloidal tungsten, or an alloy of any combination of said colloidal metals. In each case, the use of nanosized particles is preferred.

The technical name for most synthetic rubber is polychloroprene. Polychloroprene is an organic compound and it is a polymer, or long-chained molecule, formed by linking together, end-on-end, many smaller molecules or monomers which are chloroprene, $C_4H_5Cl$, the structure of which is shown below;

Polychloroprene, in either the solid or foamed processed format, in combination with the colloidal metals—specifically silver, provides an anti-microbial and anti-bacterial barrier that will inhibit infections that otherwise would normally occur when humans have open wounds or cuts or bruises to the skin while wearing wetsuits, drysuits, and the like over the exposed area of the skin. Other suitable polymers may include Hypalon, polyurethanes, polyaramids including nylons, polyesters, polycarbonates, fluoropolymers, polyolefins and various copolymers and/or blends thereof.

The use of colloidal silver and its properties is best explained by the information contained below.

The first thing to understand is that there are at least four different products on the market referred to as "colloidal silver".

The first type of product is the classic, original kind, usually called "electro-colloidal silver." This product is made either by the "electro-arc" method in deionized water, or by the "low voltage electrolysis" method in distilled water. This product is usually found in concentrations between 3-5 ppm (parts per million), but sometimes as high as 100 ppm. Properly made, this product consists of microscopic particles of pure, elemental silver suspended in water, with no other elements present. Each particle of silver carries a positive electrical charge. Colloidal silver made this way appears either transparent-clear or transparent-light yellow.

The second is known as "mild silver protein." This product chemically binds microscopic particles of silver to a protein molecule. It is usually found in concentrations between 20-40 ppm. Its appearance may be transparent-clear or amber.

The third are "silver salts." These products can be made either chemically or electro-chemically and usually create a form of silver that dissolves in the water. Concentrations range between 50-500 ppm. Its appearance is transparent-clear. The silver particles do carry a positive electrical charge, but almost invariably, these products contain other elements or compounds other than silver.

The fourth is sometimes referred to as "powdered silver." This product was developed by the Russians and is made when a pure silver wire is rapidly disintegrated by a high voltage electrical discharge, similar to an old photographic flash bulb. The microscopic silver dust is collected and either dissolved in water or added to salves and creams for topical use. Concentrations range from 100-500 ppm.

All of these products work, to one degree or another, as a broad spectrum germicide because they all contain microscopic particles of silver. That said, it is important to understand a number of things: 1) all of these products are not "colloidal suspensions" of silver, 2) these products do not all behave the same in the body or in laboratory tests, 3) effectiveness and dosage varies from product to product, 4) quality varies from product to product and from batch to batch with the same product, and 5) they are not all uniformly safe and non-toxic. There are no industry standards that manufacturers voluntarily follow to assure quality control and there is no governmental regulation of the industry.

The critical factors that make a "good" colloidal silver product are particle size, purity, concentration, and cost. The only way to authoritatively determine the first three is by laboratory analysis. The best way to determine particle size is by electron microscope photography. The best way to determine purity is by mass spectroscopy or by x-ray defraction analysis. The best way to determine concentration is by chemical analysis of total dissolved solids. The cost of the product should be calculated in reference to the total quantity of silver present, such as: $5.00/oz of 100 ppm product is equal to 25¢/oz of 5 ppm (the first has 20 times more silver by volume and costs 20 times more by volume.)

The simplest way to control these factors is to control the manufacture of colloidal silver. Without laboratory testing of commercial products, you don't know much more, because the quality control batch to batch is not well established with most brands.

The simplest way to make real colloidal silver is by the "low voltage electrolysis" method. A few batteries may be connected to some silver electrodes and placed in a glass of water. This process will cause small particles of silver to be sintered off the electrodes and enter the water. This deceptively simple method is very easy to do wrong, and many manufacturers who are making colloidal silver at home are making an inferior product.

It is very important to control the purity of the water, because the purity of the water is one of the factors that controls how small the particles of silver will be. Only high quality distilled water should be used. Use of purified or filtered water is improper because it still has too many dissolved minerals in it. Use of deionized water is incorrect because it doesn't conduct electricity well enough to start the reaction. Distilled water is just perfect to start the reaction slowly and let it proceed properly.

Another variable that influences particle size is the water temperature. The warmer the water, the faster the reaction will take place, and the smaller the resulting particles.

Silver chloride will always form if any amount of salt is present. One should never add anything to the water that will make the water conduct electricity better. Never add salt, sea salt, or Celtic sea salt to the distilled water because the salt puts chloride ions in the water that react with the silver to form silver chloride. Another serious problem arises when making colloidal silver with salt in the water. The presence of salt increases the electrical conductivity of the water and this dramatically speeds up the reaction. As the reaction speeds up under these circumstances, it produces larger particles. The product produced is invariably cloudy-white in appearance. Actual electron microscope photographs of this material show silver particles in the range of 0.05 to 0.15 microns. These particles are too large to form a colloidal suspension, and the proof is that the material will settle to the bottom of the container in a very short period of time. Therefore, this "colloidal silver" product may be dangerous to consume internally and is not desired for the present disclosure for two reasons: the presence of silver chloride and the production of large particles.

The very best voltage for the reaction is 30 volts, because the electrodes run the cleanest at this voltage. With a small power supply, set it for 30 volts. If running on batteries, it is best to start at 36 volts (three 12 volt batteries or four 9 volt batteries) and let the batteries drain down from there. Holding the silver electrodes at a uniform distance away from each other yields a better product.

When 30 volts is applied across silver electrodes held uniformly apart in distilled water, a completely different event occurs. First, the reaction proceeds very slowly. Often, for the first 15 minutes nothing seems to happen. Then finally, a faint yellow mist will begin to form. Within a few minutes, the reaction will speed up, but the particles produced will be a golden-yellow as viewed with a flashlight. Using this method, 8 ounces of distilled water at room temperature can be made into a 3-5 ppm colloidal silver preparation in 20-25 minutes. Made this way, colloidal silver can cost under 10¢/oz to make. Electron microscope photographs of this product show a silver particle size in the range 0.001 to 0.004 microns. During manufacturing, the particle cloud is a golden-yellow. These particles will hang in the water at the level they are produced, and for the most part, will not fall to the bottom of the glass. This is what a "colloidal" preparation of silver looks like. After the particles disperse, the water will look clear again, but may turn a light yellow if the concentration is high enough and after the particles have become evenly dispersed.

There has been a fair amount of controversy in the public literature concerning the appearance of the "yellow" color. A lot of well meaning people state that "yellow is bad", "silver isn't yellow", "yellow is sulfur contamination", "yellow is iron contamination", etc.

This issue is explained in a book entitled *Practical Colloid Chemistry*, published in London in 1926. In the section on the "Colours of Colloidal Metals", sub-section on the "Polychromism of silver solutions" on page 69 the following statements are made: "The continuous change in colour from yellow to blue corresponds to a change in the absorption maximum of the shorter to longer wave-lengths with a decreasing degree of dispersion. This is a general phenomenon in colloid chemistry illustrating the relation between colour aid degree of dispersion." This section goes on to describe the colors that show up in a wide variety of colloidal metal solutions. Interestingly, they all have a yellow phase. For true "electro-colloidal" silver, the particle size range that can appear yellow is 0.01 to 0.001 microns (10 to 100 angstroms) because that is the size of a silver particle that best absorbs the indigo light, leaving only its inverse color, yellow, to be observed. The final transparent-yellow appearance only shows up after the particles have become evenly dispersed.

Once achieving the making of colloidal silver particles as small as 0.001 microns, it is important to protect them. The particles stay away from each other in suspension because they each have a positive electrical charge (+) and these "like charges" repel each other. Anything that can strip this charge off the particles will degrade the quality of the colloidal silver by a process called re-coagulation, where the particles clump together again to form larger aggregates. Ultraviolet light from the sun and many plastics can cause this process to occur. Therefore, colloidal silver is best stored in dark, glass containers. The two kinds of glass container that are suitable for this are the dark amber and the cobalt blue.

The biggest "secret" about the manufacture of high quality colloidal silver is that it is nearly impossible to standardize the product. Silver is apparently reactive to a number of natural forces that have yet to be identified. Even when the voltage, the water, and the water temperature are identical, different batches will proceed at different rates on different days. The speed of the reaction can vary by over 100% depending on the day. On "normal" days, the reaction proceeds well within 15 minutes, with a visible cloud of particles. On "slow days" it may take 30 minutes before any visible production of yellow particles begins. Because of this variation, it is always wise to observe the reaction with a B flashlight to determine how quickly the reaction is occurring. Once the yellow cloud starts forming, time the batch for 5 more minutes. This is the best way to standardize the reaction.

Another controversy surrounds the question of whether this method produces "colloidal" silver or "ionic" silver. There have been discussions regarding the possibility that colloidal silver is "good" and ionic silver is "bad." The word "colloidal" refers to a condition where, in this case, a solid particle is suspended in a liquid (e.g. silver in water). The solid particles are too large to be considered dissolved, but are too small to be filtered out. This colloidal condition is most easily detected by what is called the "Tyndall effect", where a narrow beam of light is shined through the liquid to produce a cone shaped dispersion of the light. The particles so illuminated also exhibit a random, zig-zag activity called "Brownian motion" when observed under a microscope. When something is completely dissolved, both the Brownian and Tyndall effects disappear.

The word "ionic" refers to a condition where a particle has an electric charge. In the case of "electro-colloidal" silver, this electric charge is always positive. Silver will not form a negatively charged ion. So, factually electro-colloidal silver is both colloidal and ionic. It is considered colloidal because of the particle size and it is considered ionic because of the particle charge. In fact, most of the biological studies suggest it is colloidal silver's ionic characteristics that make it such a good germicide. It is also interesting to note that older chemistry text books make no distinction between the colloidal and ionic states of the electro-colloidal metals.

The quality of the finished product depends entirely on the purity of the water you start with and the purity of the silver you start with. Most of the current literature suggests that only 99.9999% pure silver can be used. Most home systems use 99.9% pure silver. To determine the difference, Academy Metals, a company in Albuquerque, N. Mex., that produces commercial silver was contacted. The total allowable impurities in 99.9% (0.999 fine) silver is 1000 ppm or 1 part in 1000. These impurities and their maximums are 1) Copper, 800 ppm, 2) Lead, 250 ppm, 3) Iron, 200 ppm, and 4) Bismuth, 10 ppm. This product is readily available in wire form and costs about $3.00 above the market (spot) price of silver. When this product is used to make electro-colloidal silver at a concentration of 5 ppm, the total impurities from the silver drop to 4 ppb (parts per billion) copper, 1.25 ppb lead, 1 ppb iron, 0.05 ppb bismuth.

99.99% silver (0.9999 fine) has total allowable impurities of 100 ppm of the same metals in the same ratios, and costs (in wire form) between $50-$90 above the spot price of silver. 99.999% silver (0.99999 fine) has total allowable impurities of 10 ppm, and in wire form costs about $250 above the spot price. 99.9999% silver, in wire form, costs more than gold and is very difficult to find commercially.

In one sample of 10 ppm colloidal silver total analysis (made with 99.9% silver electrodes), the primary impurities found were: 1) Sodium, 470 ppb, 2) Calcium, 260 ppb, 3) Manganese, 70 ppb, 4) Potassium, 50 ppb, and 5) Magnesium, 24 ppb. Since none of these impurities could have come from the silver, it suggests that the purity of the water should be of greater concern, than spending extra money on purer silver.

The concentration of silver in the water is usually measured in parts per million, or ppm. While this is the standard convention, ppm is a "ratio" and not an indicator of quantity. When a laboratory tests colloidal silver for concentration, they report the findings in milligrams per liter (mg/L). Milligrams per liter is an actual measurement of weight per volume, and therefore is a real quantity measurement. In the metric system, one liter of water weighs 1000 grams, and one milligram is one thousandth (1/1000) of a gram, so 1 mg/L is the same as 1 ppm, as long as water is the liquid. Silver weighs a little more than water, but the equivalence is very close, and the terms are often used interchangeably. With this in mind, we can calculate that one teaspoon of 5 ppm colloidal silver has about 25 mcg (micrograms) of silver in it.

In 1940, R. A. Kehoe reported that under normal circumstances, the average daily intake of fruits and vegetables would provide between 50-100 mcg of silver as a trace element. Since that time, the commercial farm soils of this country have become extremely deficient in trace minerals. For this reason, colloidal silver has also become used as a nutritional supplement. Silver can also act as a heavy metal poison in the body. It can also act as a trace mineral nutrient. The difference is in the particle size, not the concentration. Colloidal silver with a particle size of 0.001 microns has particles 100 times smaller than a preparation of silver with a particle size of 0.1 microns. The smaller the particle, the less likely it will behave as a toxin. Typically, the worst toxic reaction from metallic silver, cited in the medical literature, is a condition called Argyria. Argyria is primarily a cosmetic condition characterized by a permanent, bluish discoloration of the skin. Argyria causes no physical discomfort, and does not have any other known side effects. Your skin just looks bluish-gray. In fact, the term "blue bloods," in reference to the royal families of Europe, probably refers to a mild, argyrial condition caused by the constant eating of food from silver place settings. It is interesting to note, however, that there has never been a case of Argyria reported from the use of electro-colloidal silver, free of salts or other impurities.

In a study done, in part, by the Institute of Microbiology in Rome, Italy, and published in *Applied and Environmental Microbiology*, in December, 1992, various forms of silver were tested for their ability to kill micro-organisms. Pure electro-colloidal silver out performed silver nitrate, silver chloride, and silver sulfadiazine as a broad spectrum germicide. For all classes of bacteria, fungus, and mold samples tested, pure electro-colloidal silver worked better, and at much lower concentrations. They concluded that any additives reduced the effectiveness of the pure silver ion; the silver salts being as much as 100 times less effective.

Electro-colloidal silver's effectiveness as a broad-spectrum germicide is directly related to the number and size of the particles. The same volume of space taken up by one silver particle 0.1 microns in size, will hold about 10,000 silver particles 0.001 microns in size. This reduction in particle size not only allows for a greater distribution of the silver, but it also greatly increases the total surface area of silver available for interacting with the environment. These, plus the stability of the electrical charge, are the most important factors when considering the effectiveness of colloidal silver.

While silver has been shown to be a very effective germicide, killing gram-negative bacteria, gram-positive bacteria, yeasts, molds, and viruses in laboratory experiments, this does not mean that it will invariably cure disease conditions in the body caused by these organisms. Colloidal silver is a fantastic adjunct to the home, but it is by no means a "cure-all". The biggest obstacle to using colloidal silver as a "home remedy" is the lack of information in the public domain on how to use it effectively in any given situation. The FDA has tested colloidal silver extensively and found that different microorganisms succumb to its action at a wide variety of concentrations and exposure times. If any of this information entered the public domain, the FDA would consider their own research "unsubstantiated medical claims" and reason enough to classify colloidal silver as a "new drug." The "new drug" classification would be "required" because "new use protocols" had been developed that did not exist before 1938.

Colloidal silver clearly has some extraordinary capabilities and hundreds of legitimate uses. But without standardization, quality control, and extensive medical testing, the public will never know how best to use colloidal silver in a given situation. FDA may yet try to restrict public access to colloidal silver, claiming it is unsafe, even though they know how "safe and effective" it can be when used properly. In the absence of the release of this authoritative testing data, the public is left just experimenting and groping for the answers.

Colloidal silver is apparently able to kill nearly all microorganisms, including the "friendly flora" the digestive system needs for proper function. There are a number of strategies that can reduce the probability of digestive interactions. The simplest one is to swish the colloidal silver around in your mouth for 30 seconds before swallowing. This promotes an absorption of the colloidal silver into the body away from the intestinal tract. Another strategy is to take smaller doses, multiple times per day, or with meals. Either way, if you do experience a die-off of friendly flora, they can be re-populated by taking any of the acidophilus products on the market.

Colloidal silver is an extraordinary product. It can enhance the health of humans by direct ingestion and protect humans from infections in wounds and cuts. The purchase of one of the colloidal silver makers on the market should ensure that it is the "yellow" particles colloidal silver. Any doubts about the quality of the product made or purchased can be tested at any of the following laboratories;

For particle size testing with electron microscope, contact: EMS Laboratories, 117 West Bellevue Drive, Pasadena, Calif. 91105 (818) 568-4065

For concentration test (mg/L) of total dissolved solids, contact: Associated Laboratories, 806 North Batavia, Orange, Calif. 92668 (714) 771-6900

For elemental analysis, including "Tyndall effect" and "precipitation" test, contact: Kimball Laboratories, 600 East 11800 South, Draper, Utah 84020 (801) 571-3695.

As described above, the use of silver or other metals, which are known as "cations" to reduce or eliminate unwanted bacteria or other microorganisms is well documented. Specifically, the information below further describes the benefits associated with the use of particular metal cations to achieve this effect;

TABLE 1

Summary and Description of Anti-Bacterial Agents

| Agent | Description |
|---|---|
| CATIONS | Positively charged ions with the potential to interfere with bacterial membrane function, bacterial adhesion and glucose uptake. |
| ANIONS | Negatively charged ions with the potential to interfere with bacterial membrane functions, glycolytic metabolism and glucose uptake. |
| NON-IONIC AGENTS | Non charged ions are believed to inhibit membrane enzymes which leads to reduced glucose uptake. |
| ENZYMES | Some enzymes are suggested to interfere with bacterial adhesion and others to enhance the lysozyme activity |
| SUGAR ALCOHOLS | Polyols are believed to interfere with bacterial glycolysis. |

As shown above, the cations are a single class of many possible anti-bacterial agents and their potential and activity is described in more detail here;

Cations

Substance, vehicles and concentrations

In this group of substances we find inter alia chlorhexidine, which has been known and used for about 30 years in Europe. Examples of other products that contain cations are metal ions ($Cu^{2+}$, $Zn^{2+}$ and $Sn^{2+}$, $Ag^{2+}$), alexidine (like chlorhexidine a bisbiguanide) cetyl pyridinium chloride (a quaternary ammonium compound), hexetidine (a synthetic hexahydropyridine) and sanguinaria extracts (a natural herbal extract).

A large set of references for chlorhexidine including clinical aspects are available at the I.H.C.F. server/Chlorhexidine in Dentistry and Oral Health.

Operation

Cations are attracted to the bacterial cell walls because of the substances' positive charge and the negative charge of the bacterial cell wall. Gram positive bacteria are more sensitive to cations since they are more negatively charged. Mutans streptococci are Gram positive bacteria and are therefore very sensitive to cations.

Figure 1:
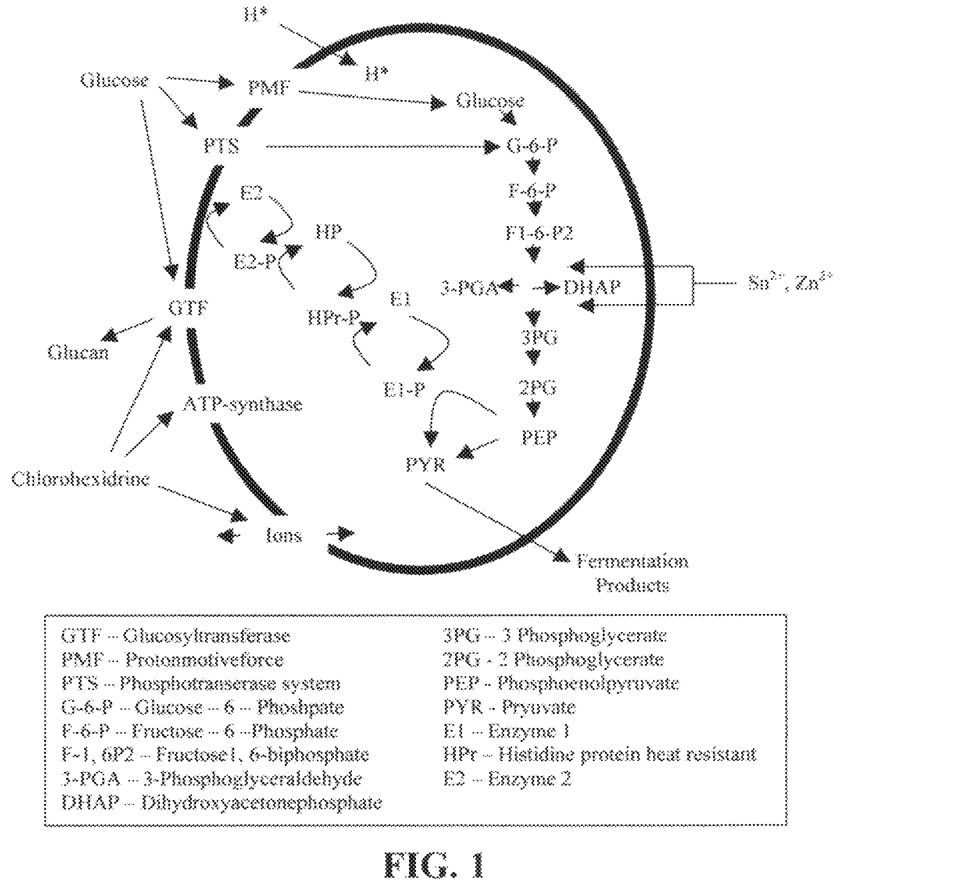
FIG. 1—A schematic of a mutans streptococcus.

Chlorhexidine, which is the most used cation in Sweden, is both hydrophilic (charged) and hydrophobic (non-charged). Because of these characteristics, chlorhexidine can affect the cariogenic mutans streptococci in different ways, as illustrated in FIG. 1. Which way of action that will dominate is also dependent on the concentration of substance. Three general effects are seen:

Disturbing the normal membrane functions of the bacteria and especially mutans streptococci.

Interfering with the bacterial adhesion on the tooth or in the pellicle by affecting a surface enzyme.

Interfering with a glycolytic enzyme which leads to a reduced acid production by the bacteria.

For review (in Swedish): Hugoson A, Koch G, Johansson S. Consensus. Klorhexidin inom tandvården. Invest-Odont, 1990.

Metal ions exhibit an additional way of action on bacteria. Two enzymes in the glycolysis may be disturbed. This leads to a reduced acid production by the bacteria.

FIG. 1. A schematic illustration of a mutans streptococcus. Seen in the illustration is the bacterial membrane with different associated enzymes like: PMF (which is influenced by a $H^+$ gradient) and PTS which both transport glucose into the bacterium, GTF which converts glucose into glucans which are important for the accumulation of mutans streptococci on the tooth surfaces, ATP-synthase which catalyzes the formation of ATP the principal carrier of chemical energy in cells and a canal through which specific inorganic ions can diffuse. Further more, the metabolic process in the bacteria is seen from glucose to fermentation products.

The operating action of chlorhexidine in general on mutans streptococci and further actions by metal ions are seen in the figure. The effect on the metabolic process inside the bacteria by chlorhexidine and metallic ions is probably a consequence of membrane breakdown.

Efficacy

The most frequently used substance in the cation group from a professional point of view is without any doubt chlorhexidine. Since it is the substance that best fulfil the demands of disturbing the membrane functions, being plaque-reducing and inhibiting the metabolism, chlorhexidine is also being used as a reference when other cationic agents are compared concerning their efficacy.

The duration of effect depends on the concentration and substantivity of the agent but also on the selection of vehicle.

Wetsuit, drysuit and other water garment construction using a composite with colloidal or nanosized metals—specifically micronized silver, nanoparticle sized silver and colloidal silver, is included herewithin to ensure completeness regarding the need to describe the process for developing the objects of this disclosure;

Yamamoto Corporation offers a complete line of high quality traditional and specialized high-tech neoprene materials, jerseys and coatings, as well as its own Protex Hot Melt Seam Tapes. The information supplied below is mostly from their website and describes in detail issues regarding the design and fabrication of water apparel—primarily wetsuits;

A wetsuit is a close fitting neoprene (man-made rubber) suit, the idea is to prevent the water to enter the suit. The water settles between the skin and the neoprene and the body warmth heats up that water, thus keeping the wearer warm. This will only be effective if the suit is of an excellent fit and is well made. Wetsuits are the most common thermal protection worn by divers. In water temperatures as cold as 10° or 12° and within commonly accepted recreational depth and time limits, they perform well.

Unlike dry suits, which offer protection at lower temperatures, wetsuits do not need to be equalized with compressed air to prevent suit squeeze. Minor punctures or tears are easily fixed and are not usually severe enough to stop a day's diving. Wetsuit costs less to buy and maintain than dry suit systems. They are also usually lighter to take traveling. They perform less well than dry suits as water temperature decreases and depth increases, as dive times are extended, or repetitive dives are made.

In general, you get what you pay for. As mentioned, a top quality wetsuit will cost in the range of $300.00-$500.00, but if you are only going to do a few open water swims a year, you may find you do not want to spend this sort of money and it may be wise to choose a cheaper model. Three factors for divers should determine your choice of wetsuit: planned maximum depth, anticipated water temperature it is usually cooler, the deeper you dive and work rate. For other water activities, water temperature, friction factor, and ease of movement will determine the thickness of the wetsuit or drysuit fabric. The present disclosure allows for any thickness wetsuit or drysuit fabric which accommodates the individual in their "in-water" activities. For example, instructors who spend long periods stationary while teaching entry-level courses and are acclimatized to the water temperature will often need a thicker wetsuit than a holiday diver. Acclimatization occurs most obviously for a diver making the transition from cold to warm water diving.

Tropic Suits for temperature: 25° C. to 28° C.
Wetsuit for temperature: 18° C. to 25° C.
Semi-Dry Suits for temperature: 7° C. to 20° C.

The compression ratio of the material is another important factor that determines the level of protection. Besides the technical details of the suit construction, the neoprene (polychloroprene, etc) material itself and the lamination of the material have an important influence on the quality and warmth of the suit. This is because neoprene and other elastomeric polymers have a low grade of warmth protection (low thermal coefficient). Only the gas bubbles in the material provide protection against cold, and make the material flexible and soft.

There are many different grades of polychloroprenes on the market. Choosing a good or poor polymer can increase or decrease the price of the suit by about 50%. Normally the suit is tested in the shop, but a very soft material does not at all mean that you now have the perfect suit. If the polychoroprene is too soft, then the air in the material is compressed very strongly and with increasing depth, the warmth-protection decreases dramatically. In cheaper grades of polychloroprene, not only is the air compressed very easily, but also under pressure, the cells may crack and collapse and the danger of water entry in the polymer increases. Very soft material is often not completely vulcanized. This means after some dives in greater depth, the material shrinks and produces, what is called "orange skin". Only an irresponsible manufacturer will use these materials for diving suits. Normally these kinds of materials have their market in the surface sports such as windsurfing, boating and cheaper products.

It is important to remember that as important as it is to avoid getting cold during any water activity, it is also important to avoid overheating both before and after. A hot and bothered diver is a familiar sight, and is usually the result of putting on exposure suits a long time before the dive itself. For divers, dehydration is known to increase the body's disposition to decompression sickness, as it significantly affects a diver's ability to reduce bubble formation.

Ideally a wetsuit will be made from a combination of polychroprene thicknesses not exceeding 5 mm. The thicker the suit the more warmth and buoyancy is attained, however, some people may find the thickest material will make them too buoyant. Top of the range wetsuit manufacturers have spent a lot of time researching different materials and designs to give the triathlon athlete the best possible product. All seams should be double glued and reinforced with stitching or thermal tape on the inside, or a combination of the two. This method prevents water flushing through the suit, as the seams should be watertight. Smooth skin or mesh, (black rubber on the outer side of the suit) should not be stitched on the outside seams, as this will cause the neoprene to split when stretched. The polychloroprene or other suitable polymer should feel soft and stretchy to the touch and be of a good make.

The largest organ of the human body is the skin, the key to maintaining natural temperature balance. If it is too hot, the skin absorbs sweat and thus cools the body. If it is too cold, we usually use warm clothing. Water has a much higher heat transmission than air. The body cools down to temperatures lower than 36 degrees Celsius that in certain cases will cause dangerous injuries. Diving suits are the diver's second skin. A big influence on the maintenance of body heat, which is the most important aspect when using a diving suit, is the fit of the suit. The suit must just fit on the body. Not too tight but in every, case not too loose. Every fold can contain water. In particular, arm, leg and neck openings must fit tightly. However, a suit that fits too tightly is dangerous. First, it cuts the blood circulation. Further it generates extensive stress on the material, which can lead to cell, nylon and yarn breaks, which are not covered by any guarantee. Therefore, a careful selection of raw materials combined with perfect fit of the suit to the body will provide the highest possible measure of safety for a long, enjoyable dive.

When buying a wetsuit, a water enthusiast must not only consider the correct choice for the environment but also its comfort and fit and its relationship to other equipment. An uncomfortable BCD and wetsuit combination, for example, can draw a diver's attention away from more important matters such as monitoring dive time and depth. When wearing thin warm-water suits especially, discomfort often occurs with a 'hard pack' BCD.

Other garments can be made from the composite that includes polychoropene and micronized metal cations including silver that was produced using colloidal means or other micronized silver to ensure anti-microbial activity.

Expanded Closed Cell Foam Compound Processing for Water Garments:

3-DIS (3-Dimensional Intelligent Skin)—The most up-to-date rubber technology is applied to all of Yamamoto's foam compounds. In addition to the 'Regular Carbon Black' that is generally used in rubber production, they include a special 'Spherical Carbon Black', which uniformly disperses all force loads such as stretch/elongation & pressure compression. They mix in 'FE Polymer', which prevents self-curing and induces the typical ageing process (hardening), which affects most inferior quality foam rubber compounds.

Titanium Alpha

Figure 2:
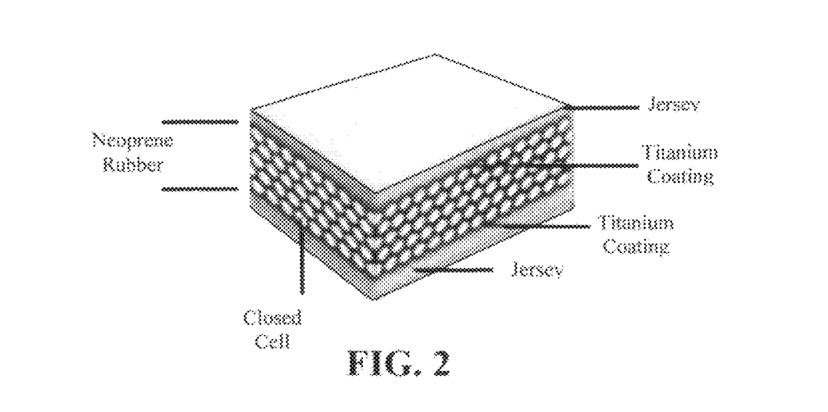
FIG. 2—Prior art embodiment with titanium.

The wetsuit concept of applying a metallic alloy barrier on neoprene surfaces to reduce body heat loss is one pioneered by Yamamoto Corp. back in the 80's, and now most leading neoprene and suit manufacturers offer "Titanium". (Ref. Detailed Description of the Drawings FIG. 2)

Figure 3:
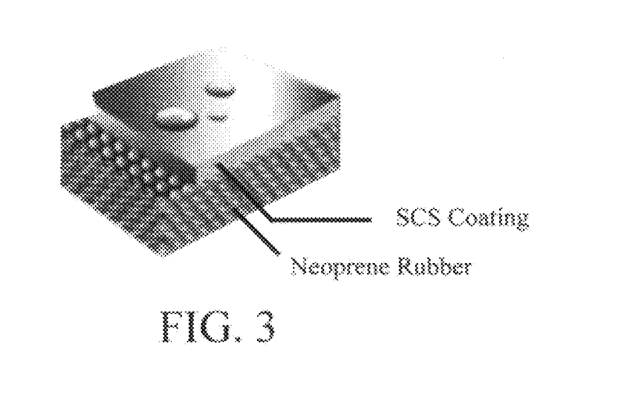
FIG. 3—Embodiment of the instant invention referred to as SCS—supercomposite skin.
Figure 4:
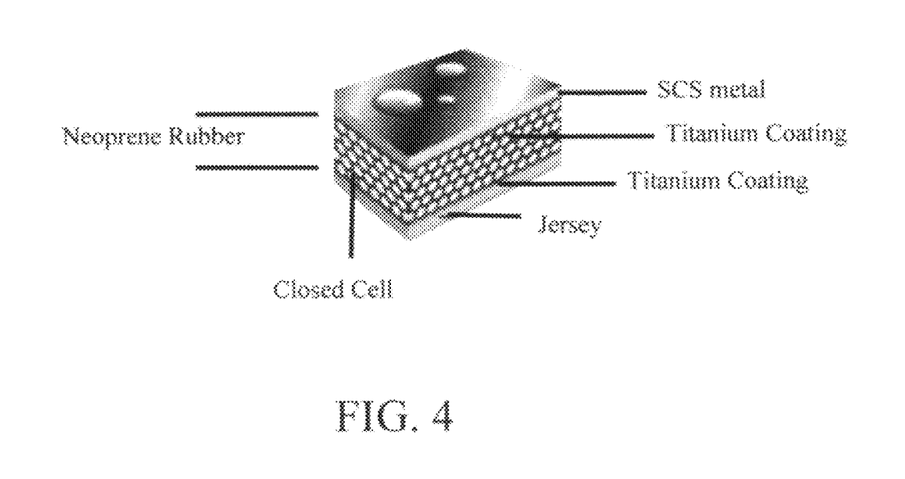
FIG. 4—Embodiment of the instant invention referred to as SCS—et al.

SCS—SUPER COMPOSITE SKIN is another new wetsuit concept pioneered by Yamamoto in the early 90's and copied by many others. SCS is a 'Low Surface Friction' coating, which allows suits to be made without an inner jersey lining, providing increased thermal insulation and extra comfort. SCS is used as the outer coating of Triathlon suits and competition swimwear, as due to its 'Hydrophobic' properties it improves swimming speeds by gliding through water more efficiently and with zero drag. Due to its ultra low surface fiction, SCS coating improves neoprene's surface abrasion resistance and strength, also making it ideal for use in neck and wrist water-stop dry seals. (Ref. FIG. 3)

Finally, SCS-METAL is a concept that has been applied to the Titanium alloy concept to SCS low friction skin, and offers ultra high thermally insulating coating in metallic silver, gold, and copper which can be applied to smooth skin, mesh skin, sharkskin (waterpile) or open cell surfaces.

The crucial independent closed cell structure offers the following advantages:

The individual foam cells do not absorb water, and each independent closed cell is filled with Nitrogen Gas, creating an excellent thermal insulation with optimum heat retaining properties. As a result of its special properties and virtually no water absorption; the weight of the material in dry or wet conditions remains almost the same and therefore wetsuits and other products made of this material do not become saturated with moisture or get heavy when submerged in water. The closed cell content of Yamamoto's Chloroprene is more than 93%, 22-33% higher than most others materials, whose closed cell content is typically in the 60-70% range.

Therefore, the most desirable fabric for water endeavors includes the following features;

Uniform Closed Cell Structure

The ratio of closed cells is over 93%. The uniform micro cellular structure ensures that if any part of the material surface is defaced or scarred, new independent concave micro cells are exposed insuring continued functionality.

High Heat Insulation & Warmth

The Nitrogen Gas enclosed in all the individual closed cells result in exceptional heat retention and efficiency.

Lightweight & Low Water Absorption

The high closed cell ratio ensures ultra low water absorption (quick drying), creating lightweight and a lower specific gravity foams with good strength and cell memory, essential qualities for wetsuit and swimwear Super Low Modulus Stretch with Optimum Cell Recovery Highest elongation with good recovery (cell memory) is 480-580% compared to that of the human skin's maximum elongation of 60-70% available at the underarm (armpit).

The outer solid skin is bonded to the foamed (closed-cell desired) at a factory. The fabric is the outside and inside layer covering the three dimension rubber sheet, that goes over the neoprene, which is what provides the comfort and strength of the high quality polychloroprene.

SUMMARY

Important characteristics for antimicrobial substances are their capability of inhibiting bacterial colonization-adhesion and their capacity to affect plaque growth-metabolic activity. They should also fulfill other demands such as, not interfering in other biological processes, being harmless towards the mucosa, and have a low toxicity, since parts of the substance may be ingested or deposited on the skin. As described above, colloidal and/or micronized silver is a perfect choice to ensure this inhibition of microorganisms and resists growth of fungus, yeast, viruses and bacteria that may be used singularly or in conjunction with sterilization, washing or application of antimicrobial agents.

There are several antimicrobial substances that can be used and with varying efficacy. "Varying efficacy" depends on many factors like vehicle, concentration, substantivity, duration of treatment and the co-operation of the patient. Again the use of colloidal metals, such as silver and other cations, has been proven effective in meeting this criteria.

The combination of a compound such as neoprene or more precisely polychloroprene together with appropriate concentrations of colloidal silver or other colloidal cations will reduce or essentially eliminate microorganism growth within and on the surface of the compound.

Accordingly, in one embodiment an objective is to provide an anti-microbial polymeric elastomer comprising micronized metals and in particular colloidal, micronized, or submicron sized silver, for apparel used in the water including; a wetsuit, a drysuit, a glove or pair of gloves, a booty or booties, a hood, a sock or pair of socks, or a rash shirt or any other garment for use in the water.

Therefore a wetsuit, a drysuit, a glove or pair of gloves, a booty or booties, a hood, a sock or pair of socks, or a rash shirt or any other garment for use in the water that includes antimicrobial colloidal micronized or submicron sized particles of silver incorporated into the resin concentrate prior to fabrication or added during the fabrication operation, such that the water garment will permit reduced antimicrobial contact, is also a subject of the disclosure.

Another objective is the addition of antimicrobial agents such as micronized, colloidal, or submicron sized particles of silver or other cations integrally formed with the water garment to resist the growth of fungus, yeast, viruses and bacteria thereon.

Another object and advantage is that the water garment with the antimicrobial agent will not require sterilization or other extensive cleansing to remove or destroy fungus, yeast, viruses and bacteria, but may be used in conjunction with other forms of antimicrobial.

It is know that micronized silver produced by Artic Silver, specifically Artic Silver 5, with the composition provided below, eliminates positive or negative bacteria including but not limited to any gram positive or gram negative bacterium such as *Pseudomonas aeruginosa, Staphylococcus aureus*, or any mold or fungus that is harmful to human health. This is a preferred composition which has been shown to be effective.

Manufacture of liquid silicone rubber mouthpieces with Arctic Silver 5 has led to reduction of Staphylococcus aureus by 99.9%. The information below describes in detail the test methodology.

The following table relates to the antimicrobial testing that was performed for liquid silicone rubber based mouthpiece according to ASTM E2180—Standard Method for Determining the Activity of Incorporated Antimicrobial Agent(s) in Polymeric or Hydrophobic Material. The ASTM method E2180 was performed, which is the method used "to evaluate (quantitatively) the effectiveness of agents incorporated or bound into or onto mainly flat (two dimensional) hydrophobic or polymeric surfaces" (Test Method E2181, pg. 1).

The test organisms utilized were Staphylococcus aureus ATCC 6538 and Pseudomonas aeruginosa ATCC 15442. Two separate agar slurries were prepared, one for each organism. The arag slurries contained 1 mL of the test organism (concentration=$7.0 \times 10^8$ cells/mL). 0.85 g NaCl, 0.3 g agar, and 100 mL of deionized water. The final inoculum concentration was equal to ~$7.0 \times 10^6$ cells/mL.

All of the samples were prepared in triplicate and aseptically cut into twelve equally sized pieces. One mL of each agar slurry was applied to the prepared samples. Using both sonification and manual vortexing the agar slurry was immediately removed from one set of the control samples and plate counts were performed. The data recovered was designated as '0 hours'.

The remaining set of control samples and the treated material was incubated at 35° C. for 24 hours with the solidified agar slurry intact. The agar slurry was again removed and processed with sonication and vortexing. Plate counts were performed. The data retrieved from this set of samples was designated '24 hours'.

Calculation of 'percent reduction' at compares the geometric mean of each time point data set with that of the relevant time point control. The results are shown in Table 1 below.

TABLE 1

Colony forming units (CFU) collected after treated and untreated polymeric mouthpieces were exposed to *Pseudomonas aeruginosa* and *Staphylacoccus aureus*. The colony forming units are based on the average of three plate counts.

| Sample Identification | | Contact Time '0 Hours' | | Contact Time '24 Hours' | | Percent Reduction | |
|---|---|---|---|---|---|---|---|
| | | *P. aeruginosa* CFU/mL | *S. aureus* CFU/mL | *P. aeruginosa* CFU/mL | *S. aureus* CFU/mL | *P. aeruginosa* | *S. aureus* |
| #1 (Control) | Avg | 50,600,000 | 37,000,000 | 516,000,000 | 312,000,000 | | |
| | GM | 46,773,514 | 35,481,338 | 501,187,233 | 281,838,293 | | |
| #2 | Avg | | | 63,600,000 | 89,600,000 | 88% | 90% |
| | GM | | | 57,543,993 | 28,183,829 | | |
| #3 | Avg | | | 43,000,000 | 3,800,000 | 95% | 99% |
| | GM | | | 20,893,961 | 1,445,439 | | |

Avg: Average of the three triplicate values
GM: Geometric Mean of the three triplicate values (used to calculate % Reduction)

Artic Silver 5 from Artic Silver, Inc., also contains sub-micron zinc oxide, aluminum oxide and boron nitride particles. The MSDS indicates the following constituents;
Silver
Boron Nitride
Zinc Oxide
Aluminum Oxide
Polyol Ester—also listed as an ester oil blend
The specification listed are as follows;
Thermal Conductance:
>350,000 W/m2° C. (0.001 inch layer)
Thermal Resistance:
<0.0045° C.-in2/Watt (0.001 inch layer)
Average Particle Size:
<0.49 microns<0.000020 inch
Extended Temperature Limits:
Peak: −50° C. to >180° C. Long-Term: −50° C. to 130° C.

These thermally-enhanced ceramic particles improve the compound's performance and long-term stability.

The invention overcomes many of the problems and shortcomings noted described in detail in the Background of the Invention section. Other objects and advantages will become obvious with the reading of the following specification and appended claims with a review of the figures.

We claim:

1. A solid or foamed rubber, synthetic rubber, or neoprene, or other suitable polymer compound; consisting essentially of; polychloroprene or other suitable polymer and at least one metal oxide or metal oxide composition of nanoparticle size, wherein said nanoparticle sized metal oxide or metal oxide composition is of a concentration within said compound that provides anti-bacterial or anti-microbial properties sufficient to retard or eliminate bacterial or microbial growth on any surface of said compound and wherein said metal oxide is the silver oxide of Artic Silver 5 or an equivalent metal oxide composition including sub-micron sized silver oxide, zinc oxide, aluminum oxide and boron nitride particles as well as a polyol ester carrier agent, wherein the thermal conductance of said metal oxide composition is greater than 350,000 W/m$^{2o}$ C. for a 0.001 inch layer of said metal composition, the thermal resistance is less than 0.0045° C.-in$^2$/Watt for a 0.001 inch layer of said metal composition, and the average particle size is less than 0.49 microns for less than a 0.000020 inch layer of said metal composition.

2. The compound of claim 1, wherein said metal oxide or metal oxide composition comprises silver, platinum, paladium, nickel, gold, aluminum, zinc, iron, copper, selenium, tungsten, or an alloy of any combination of said metals.

3. The compound of claim 1, wherein said metal oxide or metal oxide composition comprises colloidal silver, colloidal platinum, colloidal paladium, colloidal nickel, colloidal gold, colloidal aluminum, colloidal zinc, colloidal iron, colloidal copper, colloidal selenium, colloidal tungsten, or an alloy of any combination of said colloidal metals and wherein said metal oxide or metals are comprised of nanosized particles.

4. The compound of claim 1, wherein said compound together with and said metal oxide or metal oxide composition retards or eliminates positive or negative bacteria including but not limited to elimination of any gram positive or gram negative bacterium such as *Pseudomonas aeruginosa, Staphylococcus aureus*, or any other mold or fungus that is harmful to human health.

5. A wetsuit, drysuit, glove or pair of gloves, a booty or pair of booties, a hood, a sock or pair of socks, a vest, pair of shorts, or rash shirt comprising a solid or foamed rubber, synthetic rubber, or neoprene, or other suitable polymer compound comprising; primarily polychloroprene or other suitable polymer and at least one metal oxide or metal oxide composition of nanoparticle size, wherein said nanoparticle sized metal oxide or metal oxide composition is of a concentration within said compound that provides anti-bacterial or microbial properties sufficient to retard or eliminate bacterial or microbial growth on any surface of said compound used to fabricate said wetsuit, drysuit, glove or pair of gloves, a booty or pair of booties, a hood, a sock or pair of socks, a vest, pair of shorts, or rash shirt and wherein said metal oxide of nanoparticle size is the silver oxide of Artic Silver 5 or an equivalent metal oxide composition including sub-micron sized silver oxide, zinc oxide, aluminum oxide and boron nitride particles as well as a polyol ester carrier agent, wherein the thermal conductance of said metal oxide composition is greater than 350,000 W/m$^{2o}$ C. for a 0.001 inch layer of said metal composition, the thermal resistance is less than 0.0045° C.-in$^2$/Watt for a 0.001 inch layer of said metal composition, and the average particle size is less than 0.49 microns for less than a 0.000020 inch layer of said metal composition.

6. The wetsuit drysuit, glove or pair of gloves, a booty or pair of booties, a hood, a sock or pair of socks, a vest, pair of shorts, or rash shirt of claim 5, wherein said metal or said metal oxide comprises silver, platinum, paladium, nickel, gold, aluminum, zinc, iron, copper, selenium, tungsten, or an alloy of any combination of said metals.

7. The wetsuit, drysuit, glove or pair of gloves, a booty or pair of booties, a hood, a sock or pair of socks, a vest, pair of shorts, or rash shirt of claim 5, wherein said metal or said metal oxide is a colloidal metal including; colloidal silver, colloidal platinum, colloidal paladium, colloidal nickel, colloidal gold, colloidal aluminum, colloidal zinc, colloidal iron, colloidal copper, colloidal selenium, colloidal tungsten, or an alloy of any combination of said colloidal metal.

8. The colloidal metal or colloidal metal of claim 7, wherein said metal are comprised of nanosized particles.

9. The wetsuit, drysuit, glove or pair of gloves, a booty or pair of booties, a hood, a sock or pair of socks, a vest, pair of shorts, or rash shirt of claim 5, wherein said compound retards or eliminates positive or negative bacteria including but not limited to any gram positive or gram negative bacterium such as *Pseudomonas aeruginosa, Staphylococcus aureus*, or any mold or fungus that is harmful to human health.

10. A system comprising a solid or foamed rubber, synthetic rubber, neoprene, or other suitable polymeric compound; fabric comprised of a polymer compound for wearing in a wet or moist environment said compound consisting essentially of; polychloroprene or other suitable polymer and at least one metal oxide or metal oxide composition of nanoparticle size, wherein a nanoparticle sized metal oxide or metal oxide composition is of a concentration within said compound that provides anti-bacterial or anti-microbial properties sufficient to retard or eliminate bacterial or microbial growth on any surface of said compound and wherein said metal oxide of nanoparticle size is the silver oxide of Artic Silver 5 or an equivalent metal oxide composition including sub-micron sized silver oxide, zinc oxide, aluminum oxide and boron nitride particles as well as a polyol ester carrier agent, wherein the thermal conductance of said metal oxide composition is greater than 350,000 W/m$^2$° C. for a 0.001 inch layer of said metal composition, the thermal resistance is less than 0.0045° C.-in$^2$/Watt for a 0.001 inch layer of said metal composition, and the average particle size is less than 0.49 microns for less than a 0.000020 inch layer of said metal composition.

11. The system of claim 10, wherein said metal oxide or metal oxide composition comprises silver, platinum, paladium, nickel, gold, aluminum, zinc, iron, copper, selenium, tungsten, or an alloy of any combination of said metals.

12. The system of claim 10, wherein said metal oxide or metal oxide composition comprises colloidal silver, colloidal platinum, colloidal paladium, colloidal nickel, colloidal gold, colloidal aluminum, colloidal zinc, colloidal iron, colloidal copper, colloidal selenium, colloidal tungsten, or an alloy of any combination of said colloidal metals and wherein said metal oxide or metals are comprised of nanosized particles.

13. The system of claim 10, wherein said compound together with and said metal oxide or metal oxide composition retards or eliminates positive or negative bacteria including but not limited to elimination of any gram positive or gram negative bacterium such as *Pseudomonas aeruginosa, Staphylococcus aureus*, or any other mold or fungus that is harmful to human health.

* * * * *